United States Patent [19]

Fisher

[11] Patent Number: 5,179,027
[45] Date of Patent: Jan. 12, 1993

[54] METHOD EMPLOYING CHEMICAL MARKERS AND KIT FOR VERIFYING THE SOURCE AND COMPLETENESS OF URINE SAMPLES FOR TESTING FOR THE PRESENCE OF DRUGS OF ABUSE

[76] Inventor: Murray M. Fisher, 76 Braeside Road, Toronto, Ontario, Canada, M4N 1X7

[21] Appl. No.: 639,913

[22] Filed: Jan. 10, 1991

[51] Int. Cl.$^5$ .................................. G01N 37/00
[52] U.S. Cl. ..................... 436/56; 128/630; 422/61; 424/9; 436/183; 436/901
[58] Field of Search ............ 436/56, 174, 180, 183, 436/901; 422/61; 128/630, 749, 760, 771; 424/2, 9

[56] References Cited

U.S. PATENT DOCUMENTS

| | | | |
|---|---|---|---|
| 4,215,197 | 7/1980 | Tarbutton | 435/18 |
| 5,039,616 | 8/1991 | Copelan | 436/56 |

*Primary Examiner*—Robert J. Hill, Jr.
*Attorney, Agent, or Firm*—W. Thad Adams, III

[57] ABSTRACT

The present invention relates to a method and a kit for verifying the source and completeness of urine samples when collected for testing for the presence of drugs of abuse. The method involves observing an individual consume (1) a quantity of a first chemical marker reagent capable of confirming upon chemical analysis the completeness of the urine sample and (2) a quantity of a second chemical marker reagent capable of confirming upon analysis the accuracy of the source of the urine sample. The urine subsequently collected is analyzed by known analytical techniques.

6 Claims, No Drawings

METHOD EMPLOYING CHEMICAL MARKERS AND KIT FOR VERIFYING THE SOURCE AND COMPLETENESS OF URINE SAMPLES FOR TESTING FOR THE PRESENCE OF DRUGS OF ABUSE

The present invention relates to a method for verifying the source and completeness of urine samples when collected for testing for the presence of drugs of abuse.

Currently, there are a number of government departments, including defense and transportation, which require that new and current employees be tested for the presence of drugs of abuse. Typically such testing is carried out on a urine specimen received from the individual to be tested. Such urine testing is becoming more commonplace due to legislation, as well as an increased awareness in various industries of the importance of identifying users of drugs for the purpose of avoiding potential legal liability due to accidents, injuries, damage to property, etc. It is believed that any safety intensive industry will in the future, be testing employees for drug use.

The only practical means currently available for testing for the presence of drugs of abuse is to analyze an individual's urine sample for the presence of such drugs or metabolites thereof. Methods for analyzing urine samples for the detection of drugs of abuse are known. There exists however, a problem with the collection of urine specimens to be subjected to such testing. Given the consequences of a positive finding for the presence of drugs of abuse in an individual's urine, the integrity and completeness of urine samples submitted for testing are themselves subject to manipulation and abuse. For example, individuals have been known to submit for testing, urine samples which have been adulterated. Such adulteration has included the addition of foreign substances to the urine, as well as the dilution of the urine for the purpose of hiding the presence and concentration of drugs of abuse (or relevant metabolites) which may be present in the urine.

As a result, in the United States, urine collection is frequently watched by an observer in a urine collection facility. Such observation is however offensive to many as an affront to civil rights and liberties. Consequently, there has been a tremendous amount of pressure on governments and other agencies to collect urine samples for testing for drugs of abuse, in a manner which does not offend human rights and liberties. However, failure to watch the urine being collected results in no assurance that the urine ultimately tested did in fact originate from the person offering it as a sample. For example, if the urine collection was not observed, a user of drugs of abuse could fraudulently offer as his or her urine sample the urine of a friend or other individual who has not used any drugs.

Furthermore, even under circumstances where the collection of the urine specimen is observed by an employee of a testing facility, there still remains some potential for abuse. In particular, and again in view of the serious consequences of failing such a drug test, individuals have been known to introduce via catheter, into their bladders, the urine of another person, so as to attempt to fraudulently pass the testing. In those cases, even when urine collection is observed, there is no assurance that the urine excreted was secreted by the individual providing the sample.

The problems with prior art methods for collecting urine samples for testing for drugs of abuse may be summarized as follows. Observing the urine being collected has been regarded by some as a serious invasion of privacy. Providing for the observation of urine samples being collected, has required elaborate collection facilities. Notwithstanding the observation of urine collection, adulteration of urine samples is still possible. Lastly, a single collection has not on occasion been sufficient, when analyzed, to be representative of metabolites being secreted in a given individual.

In view of the aforesaid, there is a serious need for a method for verifying the source and completeness of urine samples when collected for testing for the presence of drugs of abuse. The presence of an incomplete urine sample may provide misleading results when tested. Furthermore, the testing of urine from a third party or the testing of an adulterated sample may result in totally false results.

In order to circumvent the aforesaid problems and disadvantages, the inventor herein has devised a method for assuring, within reasonable limits, the accuracy of the source and completeness of urine samples collected for testing for drugs of abuse.

In the broadest embodiment, the present invention provides a method for verifying the source and completeness of urine samples, (not necessarily for testing for the presence of drugs of abuse) comprising: observing an individual consume a quantity of a first chemical marker, quantitatively excreted in the urine, said first chemical marker capable of confirming upon chemical analysis the completeness of the urine sample; observing the individual consume a quantity of a second chemical marker, secretable in measurable amounts in the urine, said second chemical marker capable of confirming upon chemical analysis the accuracy of the source of the urine sample; requiring the individual to collect a urine sample within a period of time from said consumption sufficient to allow requisite quantities of the first and second chemical markers to be secreted in the urine; documenting the time at which and quantity and identity of the chemical markers consumed as well as the identity of the individual; subsequently analyzing the collected urine by known analytical techniques to determine the quantities of the first and second chemical markers therein so to be able to verify the source and completeness of the urine sample in relation to the information documented.

The present invention also provides for a kit for use in verifying the source and completeness of urine samples, also not restricted to testing for the presence of drugs of abuse, comprising; a container for collecting a urine sample; and a fluid containing a quantity of a first chemical marker quantitatively excreted in the urine, said first chemical marker capable of confirming upon chemical analysis the completeness of the urine sample, and a quantity of a second chemical marker secretable in measurable amounts in the urine, said second chemical marker capable of confirming upon chemical analysis the accuracy of the source of the urine sample.

The method of the present invention permits individuals to collect their own urine specimens in privacy, for example in their own homes. The present invention provides for the individual to be tested, to consume chemical marker reagents which are safe and are secreted quantitatively in the urine within six to eighteen hours (or other reasonably short period of time) following ingestion. Subsequent analysis of the urine for the chemicals permits confirmation of the urine sample coming from the person identified as ingesting the markers as well as confirmation of the completeness of the urine sample collected. Employing the method of the present invention requires observation and documentation of the individual ingesting the chemicals. The present method contemplates employing a variety of combinations of chemical marker reagents, and recording the particular combination ingested, so as to reduce very significantly the risk of two individuals being tested, switching and/or mixing their urine samples.

The present invention contemplates the individual to be tested, ingesting as part of a flavoured fluid drink or otherwise, a recorded amount of chemical marker reagents such as PABA, an analog thereof or one of its salts and creatinine labelled with a non-radioactive stable isotope. The chemical marker reagents may be made identifiable only to the laboratory conducting the tests, by having the container(s) housing the reagents, bar or number coded. The identity of the specific reagents consumed by any one individual would not under such circumstances be known to the person being tested or to the person documenting matters associated with the performance of the test. Not revealing the identity of the marker reagents to the employee or person involved in supervising the consumption of marker reagents serves to reduce further the possibility of fraudulent activity for the purpose of registering a false negative.

PABA which is a "B" vitamin, is water soluble and is completely safe to ingest. The PABA, an analog thereof (such as m-aminobenzoic acid or o-aminobenzoic acid) or one of its salts (e.g. sodium, potassium or diethylamine) may be provided in a variety of doses of for example 100, 200, 300, 400, 500 up to 2,000 milligrams. The creatinine which may be administered in a trace amount (as long as the label or tag may be accurately detected) and which is entirely secreted by the kidneys, may be tagged with one or more of C-13, N-15, deuterium oxide ($D_2O$) or O-18 or other safe labelling agent. Accordingly, an individual to be tested would receive one of many possible doses of PABA or an analog thereof (or one of its salts) combined with one of potentially several, differently labelled doses of creatinine. Alternating the doses and combinations given to individuals from amongst the aforesaid variables should reduce to an almost insignificant level, the risk of two individuals receiving the identical combination of doses of chemical marker reagents and thereafter switching urine samples prior to analysis. In order to increase further the number of variables, and hence reduce the risk, it is also possible to label or tag the PABA, the analog thereof or its salts by various means known in the art.

The method of the invention may be employed as follows. The individual subject to be tested would attend at a facility immediately after having voided. Alternatively the individual could be requested to void his or her bladder upon arrival at the facility. An attendant would document the identity of the individual. Thereafter, the individual would be presented with a flavoured drink containing a combination of the aforesaid chemical marker reagents and observed while consuming the drink. Subsequent to consumption, an attendant at the facility would document the time of the consumption, the identification code for the specific chemical markers and quantities present in the flavoured drink and would initiate the appropriate chain of custody of that individual. There is flexibility in the manner in which the pertinent information is documented. The information concerning the identity or amount of the chemical marker reagents would of course not be disclosed to the individual being tested.

The individual subject would then receive a collection kit including a vessel ($1 \times 1,000$ ml., $1 \times 500$ ml. or $2 \times 500$ ml.) to be used for collecting a urine sample within the following twenty-four hours. The exact period of time within which the urine sample must be collected will depend on the specific chemical markers to be used, although it is contemplated that suitable markers will be quantitatively secreted into the urine, within approximately six to eighteen hours following consumption. The individual may thereafter take the collection kit home and in the privacy thereof, collect a urine specimen.

Subsequent to collecting a urine sample, the individual would be requested to re-attend at the testing facility for the purpose of delivering the urine sample and furthermore to have the volume etc. of the sample as presented, documented. Generally the individual would be asked to return twenty-four hours after consumption of the marker reagents, although the urine may be tested after longer periods of time assuming it is properly stored (e.g., in refrigerator).

The collected urine specimen may then be subjected to a pre-screening test for drugs of abuse, using one of a number of known immunoassay or chromatographic techniques. The purpose of the pre-screening is to quickly determine which samples are clearly negative and hence need not be further tested. For samples providing positive results in respect of drugs of abuse (at the pre-screening stage) such results may be confirmed by the use of more sophisticated and sensitive techniques such as gas chromatography/mass spectroscopy (GS/MS). The verification of the accuracy and the source of the urine sample may be performed shortly after the urine is subjected to the pre-screening.

The completeness of the collection sample may be confirmed based on the percentage of the ingested PABA, an analog thereof or a salt thereof (or other marker which is almost exclusively secreted in the urine within twenty-four hours) present in the urine sample. Statistically, recoveries of less than 85% of PABA metabolites would be obtained from only 5% of individuals making complete collections. Therefore, in the general population, collections containing less than 85% should be considered incomplete and a repeat collection should be obtained. The amount of the stable isotope of creatinine (or other suitable marker) present in the urine will assist in confirming that the urine sample has not been diluted with either urine or water. Alternatively, analysis of electrolytes, specific gravity or pH may be used to assess other types of adulteration. It is also possible to monitor adulteration by checking for the presence of trace elements or constituents normally found in the urine.

The advantages of the present method are several. The main advantage is the lack of invasion of the privacy of the individual subject to be tested. In addition, although the individual to be tested still has to attend twice, the method of the present invention is faster and more convenient for the employees and the facility engaged in the testing. The chain of custody of the urine involves the individual to be tested, in that the individual is responsible for the integrity of the urine sample before returning it to the collection centre. The timing and volume of urine collected are not critically important. The present method is totally safe and may be employed to process a large number of individuals. Furthermore, the present method detects fraudulent dilution of urine with water or addition of someone else's urine. Further still, no specific collection centre or facility is required.

The present invention also contemplates the provision of a kit which includes a collection bottle as well as the prepackaged fluid drink containing specific amounts of chemical marker reagents, known to the testing facility, while not known to the individual subject being tested. Such kits could be employed by testing facilities in large numbers. Alternatively, the kits may be used without resort to a specific facility, providing ultimate access to chemical analytical equipment is possible. The kits may also include pre-printed forms to assist in the documentation of the ingestion of the chemical markers and the return of the sample collected.

Although PABA, an analog thereof or its salts, and creatinine have been specifically identified as safe chemical marker reagents, other chemicals, also safe and quantitatively secreted in the urine may be used. One example is urea. Others which may be used are known to those skilled in the art of analytical testing of urine and include for example certain amino acid sugars.

In addition, it should be recognized that the principle of the present invention as well as the specific method described herein may be used beyond the field of testing for the presence of drugs of abuse. The method of the present invention may also be employed in a variety of types of clinical drug trials which are monitored based on testing the urine of the individuals who are involved in the trials. Applying the present invention will provide a method for confirming the source and completeness of the urine samples which must be tested in such clinical trials.

A flow chart illustrating the application of the present invention together with Standard Operating Procedures (SOP) follows.

FLOW CHART

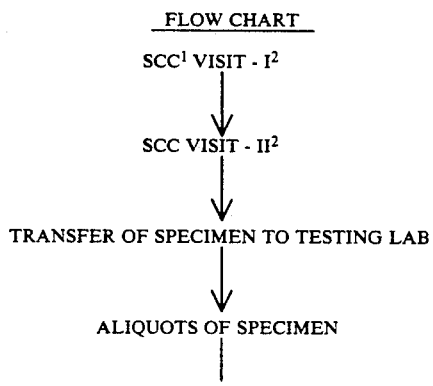

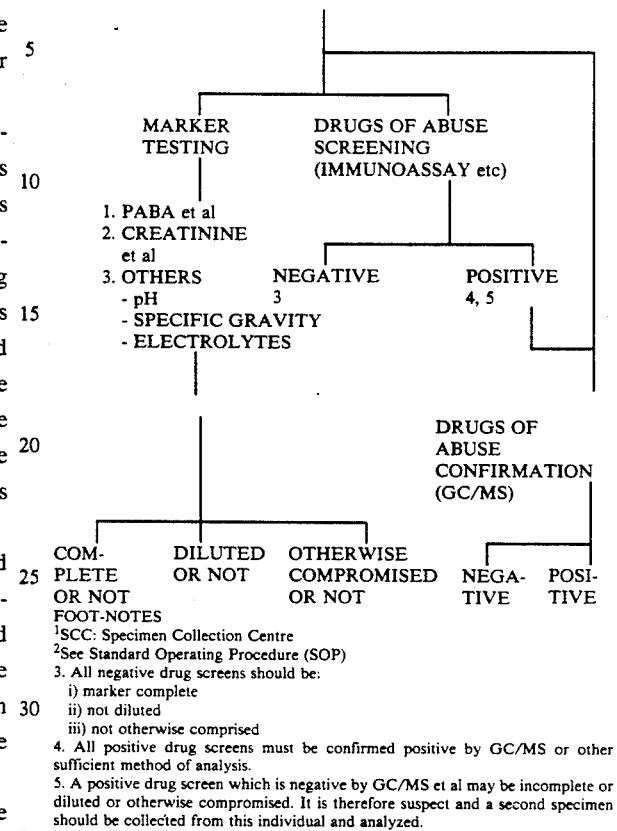

FOOT-NOTES
[1]SCC: Specimen Collection Centre
[2]See Standard Operating Procedure (SOP)
3. All negative drug screens should be:
  i) marker complete
  ii) not diluted
  iii) not otherwise comprised
4. All positive drug screens must be confirmed positive by GC/MS or other sufficient method of analysis.
5. A positive drug screen which is negative by GC/MS et al may be incomplete or diluted or otherwise compromised. It is therefore suspect and a second specimen should be collected from this individual and analyzed.

---

STANDARD OPERATING PROCEDURES (SOP)
URINE COLLECTION

VISIT - I To specimen collection centre (SCC)
1. Please attend the SCC:
   Room _____
   Address _____
   Telephone Number _____
   Time _____
   Date _____
2. Please VOID (empty your urinary bladder completely) immediately before you come to the SCC.
3. Please bring with you some PICTURE IDENTIFICATION and your SOCIAL INSURANCE NUMBER.
4. You will be expected to do the following:
   i) sign the accompanying consent form;
   ii) swallow a specifically assigned coded volume of a completely safe solution containing chemical markers which will verify the source, completeness and integrity of your urine sample;
   iii) receive a urine collection kit containing the following:
      a) chain of custody form,
      b) urine collecting vessel,
      c) urine collecting aid (females only),
      d) urine collecting instructions; and
   iv) sign the chain of custody form and container labels.

VISIT - II To Specimen Collection Centre (SCC)
1. Please attend the SCC:
   Room _____
   Address _____
   Telephone Number _____
   Time _____
   Date _____
2. Please bring with you some PICTURE IDENTIFICATION and your SOCIAL INSURANCE NUMBER.

| STANDARD OPERATING PROCEDURES (SOP) URINE COLLECTION |
| --- |
| 3. You will be expected to do the following:<br>  i) return all components of the urine collection kit;<br>  ii) sign the chain of custody document;<br>  iii) initial the specimen labels which will include the following information:<br>    a) SCC identification,<br>    b) your identification number,<br>    c) date and time of your urine collection,<br>    d) approximate volume of urine collection,<br>    e) your initials to identify and acknowledge the specimen as urine and only urine and only of your origin,<br>    f) specimen number linking the urine specimen and the transfer invoice.<br>  iv) observe the packaging and sealing of your specimen of urine in its shipping container and to initial that container. |

The embodiments of the invention in which an exclusive property or privilege is claimed are defined as follows:

1. A method for verifying the source and completeness of a urine sample comprising:
    (a) observing an individual consume a quantity of a first chemical marker quantitatively excreted in urine, said first chemical marker capable of confirming upon chemical analysis the completeness of a urine sample;
    (b) observing the individual consume a quantity of a second chemical marker secretable in measurable amounts in urine, said second chemical marker capable of confirming upon chemical analysis the accuracy of the source of a urine sample;
    (c) requiring the individual to collect a urine sample within a period of time from said consumption sufficient to allow requisite quantities of the first and second chemical markers to be secreted in the urine;
    (d) documenting the time, quantity and identity of the chemical markers consumed as well as the identity of the individual;
    (e) subsequently chemically analyzing the urine sample by known analytical techniques to determine the quantities of the first and second chemical markers therein and from the determined quantities verifying the source and completeness of the urine sample in relation to the information documented.

2. The method of claim 1 wherein the urine sample is ultimately tested for the presence of drugs of abuse, said quantity of said first chemical marker is PABA, an analog thereof or one of its salts in a suitable amount and wherein said quantity of said second chemical marker is an appropriate amount of creatinine labelled with one or more of $C^{13}$, $N^{15}$, deuterium oxide ($D_2O$) or $O^{18}$ and wherein said quantities of said first and second chemical markers are consumed as part of a pre-determined amount of fluid and wherein the period of time within which the urine is collected is approximately six to eighteen hours.

3. The method of claim 2 wherein the chemical analysis of the urine sample includes measuring one or more of the specific gravity, pH or concentration of electrolytes present in the sample.

4. The method of claim 2 wherein prior to the chemical analysis of the urine sample to verify the source and completeness thereof, it is pre-screened for the total absence of any drug of abuse.

5. The method of claim 2 wherein said appropriate amount of creatinine is a trace amount and said suitable amount of PABA, an analog thereof or one of its salts is in the range of 100 to 12,000 mgs.

6. A kit for use in verifying the source and completeness of urine samples comprising:
    (a) a container for collecting a urine sample;
    (b) a fluid containing a quantity of a first chemical marker quantitatively excreted in urine, said first chemical marker capable of confirming upon chemical analysis the completeness of a urine sample, and a quantity of a second chemical marker secretable in measurable amounts in urine, said second chemical marker capable of confirming upon chemical analysis the accuracy of the source of a urine sample.

* * * * *